Figure 1:
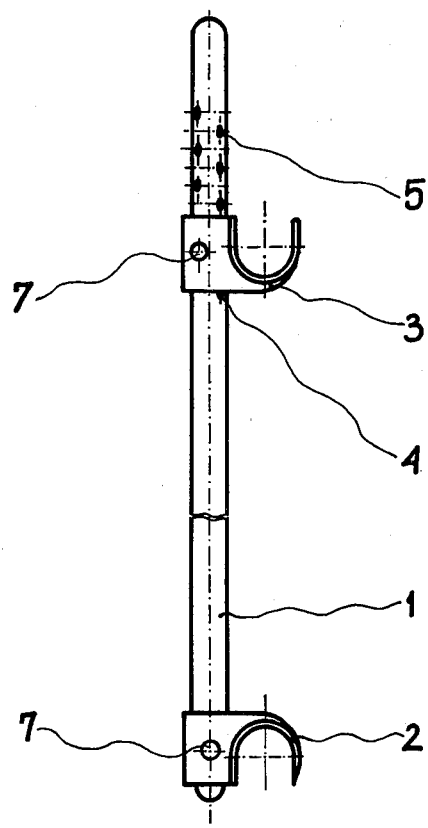

United States Patent [19]

Bacal et al.

[11] 4,369,770

[45] Jan. 25, 1983

[54] SURGICAL STRUT FOR TREATMENT OF THE BACK-BONE

[75] Inventors: Kazimierz Bącal, Góra; Lech B. Wierusz, Swiebodzin; Janusz Miszczyk, Zielona Góra, all of Poland

[73] Assignee: Wyzsza Szkola Inzynierska Im. J. Gagarina, Zielona Góra, Poland

[21] Appl. No.: 285,698

[22] Filed: Jul. 22, 1981

[30] Foreign Application Priority Data

Jul. 30, 1980 [PL] Poland .................................. 226000

[51] Int. Cl.³ ............................................. A61F 5/01
[52] U.S. Cl. ............................. 128/69; 128/92 R; 128/92 E
[58] Field of Search .................. 128/69, 68, 75, 78, 128/92 R, 92 E

[56] References Cited

U.S. PATENT DOCUMENTS

| | | | |
|---|---|---|---|
| 4,257,409 | 3/1981 | Bacal et al. | 128/69 |
| 4,269,178 | 5/1981 | Keene | 128/69 |
| 4,271,836 | 6/1981 | Bacal et al. | 128/69 X |

FOREIGN PATENT DOCUMENTS

| | | | |
|---|---|---|---|
| 2729160 | 1/1978 | Fed. Rep. of Germany | 128/69 |
| 2244446 | 4/1975 | France | 128/69 |
| 2289164 | 5/1976 | France | 128/69 |
| 96695 | 10/1978 | Poland | 128/69 |

OTHER PUBLICATIONS

Scoliosis–Design and Specifications of Instrument, by P. R. Harrington (paper) pp. 3, 27, 28 and 41, 1968.

*Primary Examiner*—Ronald L. Frinks
*Attorney, Agent, or Firm*—Ladas & Parry

[57] ABSTRACT

The subject of the invention is a surgical strut for treatment of the back-bone.

The strut has a rod having a round cross section provided at one end with a number of through holes disposed perpendicularly to the rod axis. The axes of neighboring holes form an angle of 90°. Said holes are aimed at fitting a pin fixing the position of the hook, mostly the pectoral one, mounted on the rod. Said hook is provided with a round hole the wall whereof is from the side of the front face provided with four recesses disposed on the periphery every 90°, constituting the seats for the pin.

In order to maintain a suitable elasticity the rods of the struts having the lengths smaller than 250 mm have a differentiated diameter the dimension whereof in relation to the rod length constitutes a ratio of 1:20 through 1:35. The hook co-operating with this section of the rod, mostly the lumbar hook, is provided with a blind hole wherein the rod end is supported.

3 Claims, 4 Drawing Figures

SURGICAL STRUT FOR TREATMENT OF THE BACK-BONE

This invention relates to a surgical strut for treatment of scoliosis and kyphosis, especially of juvenile ones.

The treatment of spinal curvatures is realized through an operation consisting in tensioning the back-bone and holding it in the state of prolonged stress over a period of at least a dozen or so months. For the purposes of the therapy pull springs are employed commonly, for struts, or distractors being technically most perfect devices, especially Harrington distractors, as well as struts with hook catches.

The Harrington distractors are built of a bar having a round cross-section, and at one of the ends are provided with conical-and cylindrical steps aimed at hitching the pectoral hook in a suitable distance from the lumbar hook attached at the other end of the rod. The surgical struts according to the Polish Patent Specification No. 96 659 are also made of a round bar, being at one end provided with several radial grooves aimed at fitting the stopper ring whereupon the pectoral hook rests.

The distractors show a number of disadvantages relating both to their design and to biomechanical properties, their manufacture being difficult and labour-consuming. They show also low elasticity and often get broken in the patient's organism, producing a danger for his health and life. Known surgical struts are characterized by higher mechanical strength, being, however, labour-consuming in manufacturing, and show low elasticity, what relates especially to struts having smaller lengths, which are too rigid.

For installation of surgical struts in the patient's organism it is employed an apparatus known from the Polish Patent Specification No. 96 695, appropriated for immediate distraction of the back-bone, provided with a screw and holders mounting the hooks, and with a dynamometer for measuring the resistance of the vertebral spine distraction.

The object of the invention is to avoid the inconveniences of known distractors and surgical struts, and its task consists in providing a design of a surgical strut simple in manufacture, showing a relatively high elasticity independently of its length, and being easily installable by the surgeon.

Said object has been achieved through providing a design of the surgical strut provided with a pectoral hook and a known lumbar hook, wherein in the upper portion of the rod a number of holes is made, being disposed perpendicular to the axis, aimed at fitting a thrust pin, whereby the axes of neighbouring holes form the angle of 90°. Against the protruding ends of the thrust pin one of the hooks abuts, preferably the pectoral one, being in one of the front faces provided with seats for the thrust pin, having the form of four recesses disposed on the periphery of the opening wherein the rod is introduced, every 90°. In order to maintain a constant slenderness ratio, and to increase the elasticity of the rods of struts having suitable required lengths, the shorter struts, having the length less than 250 mm, show a reduced diameter on the section of the rod being not provided with holes. The ratio of said diameter to the length of the rod equals to 1:20 through 1:35. The hook, preferably the lumbar one, co-operating with this end of the slender-made rod has a blind hole wherein the rod end abuts.

The surgical strut according to the invention is characterized by a constant slenderness ratio independently of the required rod length, and eliminates the superficial grooves and retainer rings, decreasing its fatigue strength, or requiring to be strengthened. The new design facilitates the displacing of the pectoral hook along the strut rod with simultaneous elimination of the possibility of wedging of the installed and loaded hook in the groove of the rod, especially at performing an additional correction by means of the device according to the U.S. Pat. No. 4,271,836.

Figure 2:
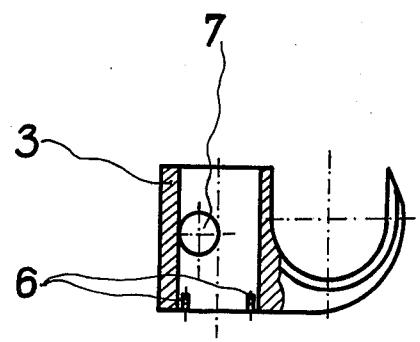
Figure 3:
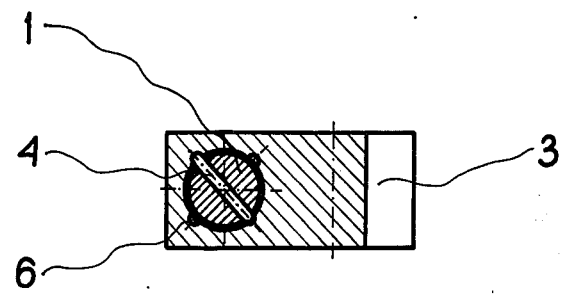
Figure 4:
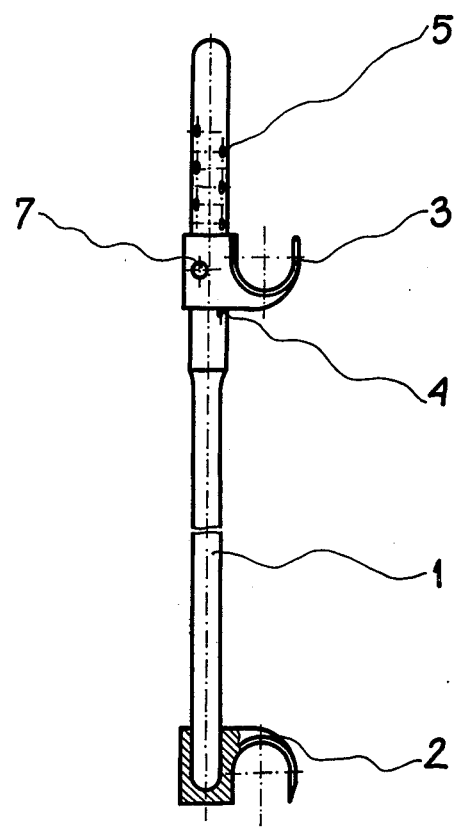

The surgical strut according to the invention is shown in an exemplary embodiment in the accompanying drawing wherein FIG. 1 is a side view of the strut with hooks, FIG. 2 is a side view in half-section of the hook, FIG. 3 is the cross-sectional view of the surgical strut at the place where the thrust pin passes through the strut rod, and FIG. 4 is a side view of the slender-made strut with hooks.

The surgical strut according to the invention is made of a bar 1 having a round cross-section. At one end of the rod 1 the lumbar hook 2 is fitted, mounted in a fixed position on the neck of the rod 1. At the other end of the rod 1 the pectoral hook 3 is mounted the position whereof is fixed by means of the thrust pin 4. Said pin is mounted in one of chosen through holes 5 the axes whereof are perpendicular to the axis of the rod 1. Said holes 5 are disposed this way on the length of said rod that the axis of each next hole is perpendicular to the axis of the preceding hole. The pectoral hook 3 fitted at the end of the rod 1 is from one front side, in the plane perpendicular to the hole axis, provided with four perpendicular to each other recesses 6 made in the hole wall. Said recesses 6 are aimed at mounting the thrust pin 4, located in the hole 5 of the pin 1, and thus at fixing the position of the hook 3 on the rod 1. the holes 7 made in the hooks 2 and 3 are aimed at mounting it in the distraction apparatus according to the Polish Patent Specification No. 96 695. In order to maintain an equal elasticity of struts having various lengths, the struts having the length smaller than 250 mm have a slender-made section in the portion being not provided with holes, as shown in FIG. 4. The lumbar hook 2 wherein the slender-made end of the strut 1 is installed has a blind hole constituting a bearing surface for this end of the strut.

What is claimed is:

1. A surgical strut for treatment of the back-bone, consisting of a rod having a round cross-section, and of hooks mounted thereon, characterized by that at one end of the rod (1) it is provided with a number of through holes (5) perpendicular to the rod axis, aimed at mounting a thrust pin (4), whereby the axes of neighbouring holes form an angle of 90°, and one of the hooks (3) is from the side of the front face provided in the wall of the round hole with four recesses disposed on the periphery of the hole every 90°, constituting the seats for the thrust pin (4).

2. A surgical strut as defined in claim 1, characterized by that one of the hooks is provided with a blind hole.

3. A surgical strut as defined in claim 1, characterized by that the ratio of the diameter of the rod (1) to its length amounts 1:20 through 1:35.

* * * * *

UNITED STATES PATENT AND TRADEMARK OFFICE
CERTIFICATE OF CORRECTION

PATENT NO. : 4,369,770

DATED : January 25, 1983

INVENTOR(S) : Kazimierz BACAL et al

It is certified that error appears in the above—identified patent and that said Letters Patent is hereby corrected as shown below:

Title Page, item [75], line 1    before "Gora" add --Zielona--.

Signed and Sealed this

Third Day of May 1983

[SEAL]

Attest:

GERALD J. MOSSINGHOFF

Attesting Officer    Commissioner of Patents and Trademarks